US012730237B2

(12) United States Patent
Takayasu

(10) Patent No.: US 12,730,237 B2
(45) Date of Patent: Sep. 8, 2026

(54) DETECTOR MODULE UNIT, RADIATION DETECTOR, AND X-RAY COMPUTED TOMOGRAPHY APPARATUS

(71) Applicant: Canon Kabushiki Kaisha, Tokyo (JP)

(72) Inventor: Masao Takayasu, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 152 days.

(21) Appl. No.: 18/669,796

(22) Filed: May 21, 2024

(65) Prior Publication Data

US 2025/0067888 A1 Feb. 27, 2025

(30) Foreign Application Priority Data

Aug. 23, 2023 (JP) ................................ 2023-135430

(51) Int. Cl.
*G01T 7/00* (2006.01)
*A61B 6/03* (2006.01)
*G01T 1/17* (2006.01)

(52) U.S. Cl.
CPC ................ *G01T 7/00* (2013.01); *A61B 6/035* (2013.01); *G01T 1/17* (2013.01)

(58) Field of Classification Search
CPC ........... G01T 1/17; G01T 1/244; G01T 1/243; G01T 1/24; G01T 7/00; A61B 6/035
See application file for complete search history.

(56) References Cited

U.S. PATENT DOCUMENTS 7,342,234 B2 * 3/2008 Yanagita ................ G01T 1/244 250/370.15
9,513,236 B2 * 12/2016 Kawaguchi ............ A61B 6/032
11,550,069 B2 * 1/2023 Yu .......................... A61B 6/032
2005/0161608 A1 * 7/2005 Heismann ............ H10F 39/189 250/370.09
2006/0241386 A1 * 10/2006 Yanagita ................ G01T 1/249 600/415
2009/0067571 A1 * 3/2009 Lacey ...................... A61B 6/06 378/19
2013/0221468 A1 * 8/2013 Bolognia ............... H10F 77/60 257/433

(Continued)

FOREIGN PATENT DOCUMENTS

JP 2002-344180 A 11/2002
JP 2006-284394 A 10/2006

(Continued)

*Primary Examiner* — David J Makiya
*Assistant Examiner* — Soorena Kefayati
(74) *Attorney, Agent, or Firm* — Oblon, McClelland, Maier & Neustadt, L.L.P.

(57) ABSTRACT

A detector module unit according to an embodiment includes a detecting element array, signal processing circuitry, a holding plate, and a casing. In the detecting element array, a plurality of detecting elements each configured to convert radiation into an electrical signal are arranged. The signal processing circuitry is configured to process the electrical signals. The holding plate is configured to hold the detecting element array and the signal processing circuitry. The casing is thermally connected to the signal processing circuitry and has a first face and a second face opposing each other while the holding plate is interposed therebetween. The first face and the second face of the casing each have a fin.

8 Claims, 8 Drawing Sheets

(56) References Cited

U.S. PATENT DOCUMENTS

| | | | | |
|---|---|---|---|---|
| 2015/0156920 | A1* | 6/2015 | Kawaguchi | A61B 6/4488 250/366 |
| 2016/0128651 | A1* | 5/2016 | Sugiya | A61B 6/4488 250/361 R |
| 2018/0136346 | A1* | 5/2018 | Horiuchi | G01T 7/00 |
| 2019/0072679 | A1* | 3/2019 | Ye | A61B 6/4291 |
| 2019/0350545 | A1* | 11/2019 | Ikhlef | A61B 6/4488 |
| 2021/0072410 | A1* | 3/2021 | Yu | A61B 6/4435 |
| 2021/0190978 | A1* | 6/2021 | Drago | G01T 1/244 |

FOREIGN PATENT DOCUMENTS

| | | |
|---|---|---|
| JP | 2015-104667 A | 6/2015 |
| JP | 2021-043201 A | 3/2021 |

* cited by examiner

1
X-RAY CT APPARATUS
10
GANTRY
11
16
17
13
14
P
33
12
Y
Z
X
CONTROLLING APPARATUS
15
40
CONSOLE
MEMORY
41
DISPLAY
42
INPUT INTERFACE
43
44
PROCESSING CIRCUITRY
SYSTEM CONTROLLING FUNCTION
441
PRE-PROCESSING FUNCTION
442
RECONSTRUCTION PROCESSING FUNCTION
443
IMAGE PROCESSING FUNCTION
444
30
COUCH
P
33
34
31
32
Y
Z
X
10

121
1211
1212
1213
9214

ROW DIRECTION
1214
1213
12131
X-RAYS
121
1211
CHANNEL DIRECTION
1212
12132
1214

ROW DIRECTION
X-RAYS
CHANNEL DIRECTION
121
1211
1212
1213
12131
12132
121X
121Xi
121Xo
121X
121Xi
121Xo

DETECTOR MODULE UNIT, RADIATION DETECTOR, AND X-RAY COMPUTED TOMOGRAPHY APPARATUS

CROSS-REFERENCE TO RELATED APPLICATIONS

This application is based upon and claims the benefit of priority from Japanese Patent Application No. 2023-135430, filed on Aug. 23, 2023; the entire contents of which are incorporated herein by reference.

FIELD

Embodiments described herein relate generally to a detector module unit, a radiation detector, and an X-ray computed tomography apparatus.

BACKGROUND

Conventionally, as a radiation detector used in a radiation diagnosis apparatus such as an X-ray Computed Tomography (CT) apparatus or a Positron Emission Tomography (PET) apparatus, a detector structured by arranging a plurality of detector module units is known. In such a radiation detector, because signal processing circuitry included in the detector module units generates heat as radiation is emitted, a cooling structure for cooling the signal processing circuitry is provided, generally speaking, for the purpose of preventing failures of detecting elements that may be caused by the heat generated by the signal processing circuitry.

DETAILED DESCRIPTION

Figure 1:
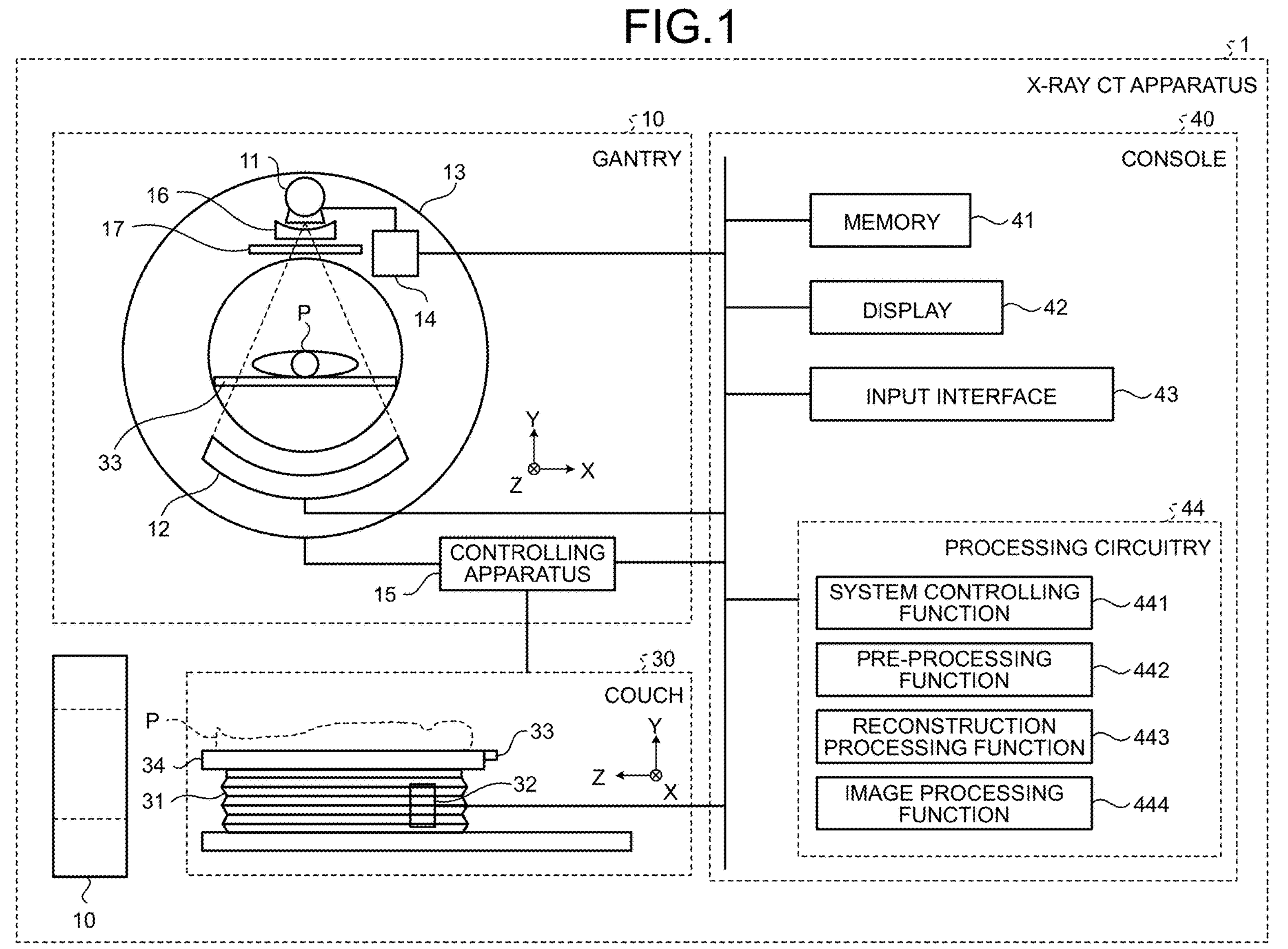
FIG. 1 is a diagram illustrating an exemplary configuration of an X-ray CT apparatus according to a first embodiment.

A detector module unit according to an embodiment includes a detecting element array, signal processing circuitry, a holding plate, and a casing. In the detecting element array, a plurality of detecting elements each configured to convert radiation into an electrical signal are arranged. The signal processing circuitry is configured to process the electrical signals. The holding plate is configured to hold the detecting element array and the signal processing circuitry. The casing is thermally connected to the signal processing circuitry and has a first face and a second face opposing each other while the holding plate is interposed therebetween. The first face and the second face of the casing each have a fin.

Exemplary embodiments of a detector module unit, a radiation detector, and an X-ray CT apparatus of the present disclosure will be explained with reference to the accompanying drawings. The configurations depicted in the drawings are schematic, and the dimensions of the constituent elements and the proportions of the dimensions among the constituent elements may be different in actuality. Further, the dimension of any single constituent element or the proportions of the dimensions among the constituent elements may be illustrated differently in different drawings.

In the following embodiments, an example will be explained in which a detector module unit and a radiation detector of the present disclosure are applied to an X-ray detector of an X-ray CT apparatus. Further, in the following embodiments, an example will be explained in which techniques of the present disclosure are applied to the X-ray CT apparatus including the detector module unit and a photon counting detector.

First Embodiment

FIG. 1 is a diagram illustrating an exemplary configuration of an X-ray CT apparatus according to a first embodiment.

For example, as illustrated in FIG. 1, an X-ray CT apparatus 1 according to the present embodiment includes a gantry 10, a couch 30, and a console 40. For the sake of convenience in the explanation, FIG. 1 depicts the gantry 10 in multiple locations.

Further, in the present embodiment, a rotation axis of a rotating frame 13 in a non-tilt state or the longitudinal direction of a couchtop 33 of the couch 30 is defined as a Z-axis direction; the axial direction orthogonal to the Z-axis direction and parallel to a floor surface is defined as an X-axis direction; and the axial direction orthogonal to the Z-axis direction and perpendicular to the floor surface is defined as a Y-axis direction.

The gantry 10 is an apparatus configured to emit X-rays onto a subject P (e.g., a patient), to detect X-rays that have passed through the subject P, and to output a result to the console 40. The gantry 10 includes an X-ray tube 11, an X-ray detector 12, the rotating frame 13, a controlling apparatus 15, a wedge 16, an X-ray limiter 17, and an X-ray high-voltage apparatus 14.

The X-ray tube 11 is a vacuum tube configured to generate X-rays by causing thermoelectrons to be emitted from a negative pole (a filament) toward a positive pole (a target), with application of high voltage from the X-ray high-voltage apparatus 14. For example, the X-ray tube 11 is a rotating anode X-ray tube configured to generate the X-rays by having the thermoelectrons emitted onto a rotating anode.

The wedge 16 is a filter for adjusting the amount of the X-rays emitted from the X-ray tube 11. More specifically, the wedge 16 is a filter configured to pass and attenuate the X-rays emitted from the X-ray tube 11 so that the X-rays emitted from the X-ray tube 11 onto the subject P has a predetermined distribution. For example, the wedge 16 is a filter obtained by processing aluminum so as to have a predetermined target angle and a predetermined thickness. The wedge 16 may be called a wedge filter or a bow-tie filter.

The X-ray limiter 17 includes lead plates or the like for narrowing down an emission range of the X-rays that have passed through the wedge 16 and is configured to form a slit with a combination of the plurality of lead plates or the like.

The X-ray detector 12 is configured to detect the X-rays that were emitted from the X-ray tube 11 and have passed through the subject P. More specifically, the X-ray detector 12 includes a plurality of detecting elements arranged in a channel direction along an arc, while being centered on a focal point of the X-ray tube 11. For example, the X-ray detector 12 has a structure in which a plurality of arrays of detecting elements are arranged in a row direction (which may be called a slice direction), while each array has the plurality of detecting elements arranged in the channel direction. In this situation, on an X-ray incident surface side of the X-ray detector 12, a collimator is provided for the purpose of reducing scattered X-rays. The collimator may be referred to as a scattered ray elimination grid or a rear collimator.

Each of the plurality of detecting element is configured to output, every time an X-ray photon becomes incident thereto, a signal that makes it possible to measure an energy value of the X-ray photon. More specifically, each of the detecting elements is structured with a plurality of electrodes and is configured, every time an X-ray photon becomes incident thereto, to output an electrical signal corresponding to the incident X-ray. For example, in the detecting elements, CZT (cadmium zinc telluride (CdZnTe)), cadmium telluride, (CdTe), germanium (Ge), or silicon (Si) may be used. Alternatively, in the detecting elements, other types of semiconductor crystals such as scintillator crystals may be used.

In other words, the X-ray detector 12 is a detector of a direct-conversion type including, as the detecting elements, semiconductor elements configured to convert the incident X-rays into the electrical signals. Alternatively, the X-ray detector 12 may be a detector of an indirect conversion type in which a fluorescent material that emits light as being excited by the X-rays is combined with an optical sensor configured to convert the light generated by the fluorescent material into an electrical signal.

Further, the X-ray detector 12 includes signal processing circuitry connected to the abovementioned plurality of detecting elements and configured to process the electrical signals output from the detecting elements. The signal processing circuitry is configured to count the photon quantity of the X-rays that have become incident to the detecting elements, by performing a pulse-height discriminating process on pulses each having a height proportional to a corresponding one of individual electric charge amounts of the electrical signals output from the detecting elements. Further, the signal processing circuitry is configured to measure energy of the counted X-rays photons, by performing a calculating process based on magnitudes of the individual electric charges. Further, the signal processing circuitry is configured to output a result of counting the X-ray photon quantity as a signal of digital data, by performing an Analog to Digital (A/D) conversion on the signals from the detecting elements. For example, the signal processing circuitry is realized by using an Application Specific Integrated Circuit (ASIC).

Further, the X-ray detector 12 includes a Data Acquisition System (DAS) configured to output detection data on the basis of the signals output from the signal processing circuitry. The DAS is configured to generate the detection data on the basis of the signal of the X-ray counted result output from the X-ray detector 12. In this situation, the detection data may be a sinogram, for example. The sinogram is data obtained by arranging the results of the process of counting the incidences to the detecting elements in various positions of the X-ray tube 11. More specifically, the sinogram is data obtained by arranging the results of counting the X-ray photon quantity in a two-dimensional orthogonal coordinate system having axes corresponding to a view direction and the channel direction. For example, the DAS is configured to generate the sinogram in units of the rows in the slice direction of the X-ray detector 12. After that, the DAS is configured to transfer the generated detection data to the console 40.

The X-ray high-voltage apparatus 14 includes: a high-voltage generating apparatus including electrical circuitry such as a transformer and a rectifier or the like and having a function of generating the high voltage to be applied to the X-ray tube 11; and an X-ray controlling apparatus configured to control output voltage corresponding to the X-ray outputs emitted by the X-ray tube 11. The high-voltage generating apparatus may be of a transformer type or an inverter type. Further, the X-ray high-voltage apparatus 14 may be provided for the rotating frame 13 (explained later) or may be provided on the side of a fixed frame (not illustrated) of the gantry 10. In the present example, the fixed frame is a supporting frame configured to rotatably support the rotating frame 13.

The rotating frame 13 is an annular frame configured to support the X-ray tube 11 and the X-ray detector 12 so as to oppose each other and to cause the X-ray tube 11 and the X-ray detector 12 to rotate by employing the controlling apparatus 15 (explained later). Further, in addition to the X-ray tube 11 and the X-ray detector 12, the rotating frame 13 further includes and supports the X-ray high-voltage apparatus 14.

In this situation, the rotating frame 13 is rotatably supported by a non-rotating part (e.g., the fixed frame; not illustrated) of the gantry 10. For example, a rotating mechanism includes a motor configured to generate a rotation driving force and a bearing configured to transmit the rotation driving force to the rotating frame 13 to cause the rotation. For example, the motor is provided in the non-rotating part, whereas the bearing is physically connected to the rotating frame 13 and the motor, so that the rotating frame 13 rotates in accordance with the rotating force of the motor.

Further, the rotating frame 13 and the non-rotating part are each provided with contactless or contact-type commination circuitry by which a unit supported by the rotating frame 13 communicates with either the non-rotating part or an apparatus outside the gantry 10. For example, when optical communication is adopted as a contactless communication scheme, the detection data generated by the DAS is transmitted, via optical communication, from a transmitter being provided on the rotating frame 13 and including a light emitting diode (LED), to a receiver being provided in the non-rotating part of the gantry 10 and including a photodiode, and is further transferred by a transmitter from the non-rotating part to the console 40. As for methods for the communication, it is possible to use, besides the method described above, other contactless data transfer methods such as a capacitive coupling method or a radio wave method, as well as a contact-type data transfer method using a slip ring and an electrode brush.

The controlling apparatus 15 includes processing circuitry having a Central Processing Unit (CPU) or the like and a driving mechanism such as a motor and an actuator. The controlling apparatus 15 has a function of receiving an input signal from an input interface 43 attached to either the console 40 or the gantry 10 and controlling operations of the gantry 10 and the couch 30. For example, upon receipt of input signals, the controlling apparatus 15 is configured to exercise control to rotate the rotating frame 13, control to tilt the gantry 10, and control to bring the couch 30 and the couchtop 33 into operation. In this situation, the control to tilt the gantry 10 is realized as a result of the controlling apparatus 15 causing the rotating frame 13 to turn on an axis parallel to the X-axis direction, on the basis of inclination angle (tilt angle) information being input by the input interface 43 attached to the gantry 10. In this situation, the controlling apparatus 15 may be provided for the gantry 10 or may be provided for the console 40.

The couch 30 is an apparatus configured to place thereon and move the subject P subject to a scan and includes a base 31, a couch driving apparatus 32, the couchtop 33, and a supporting frame 34. The base 31 is a casing configured to support the supporting frame 34 so as to be movable in vertical directions. The couch driving apparatus 32 is a motor or an actuator configured to move the couchtop 33 on which the subject P is placed in a long-axis direction of the couchtop 33. The couchtop 33 provided on the top face of the supporting frame 34 is a board on which the subject P is placed. In this situation, in addition to the couchtop 33, the couch driving apparatus 32 may move the supporting frame 34 in the long-axis direction of the couchtop 33.

The console 40 is an apparatus configured to receive operations performed by an operator on the X-ray CT apparatus 1 and to reconstruct CT image data by using the detection data acquired by the gantry 10. The console 40 includes a memory 41, a display 42, the input interface 43, and processing circuitry 44. Although an example is explained in which the console 40 and the gantry 10 are separate, the gantry 10 may include the console 40 or a part of the constituent elements of the console 40.

The memory 41 is realized by using, for example, a semiconductor memory element such as a Random Access Memory (RAM) or a flash memory, or a hard disk, an optical disk, or the like. For example, the memory 41 is configured to store therein projection data and the CT image data.

The display 42 is configured to display various types of information. For example, the display 42 is configured to output a medical image (a CT image) generated by the processing circuitry 44, a Graphical User Interface (GUI) used for receiving various types of operations from the operator, and the like. For example, the display 42 may be a liquid crystal display or a Cathode Ray Tube (CRT) display. Alternatively, the display 42 may be provided for the gantry 10, for example. Further, for instance, the display 42 may be of a desktop type or may be configured by using a tablet terminal or the like capable of wirelessly communicating with the main body of the console 40.

The input interface 43 is configured to receive various types of input operations from the operator, to convert the received input operations into electrical signals, and to output the electrical signals to the processing circuitry 44. For example, the input interface 43 is configured to receive, from the operator, a scan condition to be used at the time of acquiring the projection data, a reconstruction condition to be used at the time of reconstructing the CT image data, an image processing condition to be used at the time of generating a post-processing image from a CT image, and the like. For example, the input interface 43 is realized by using a mouse, a keyboard, a trackball, a switch, a button, a joystick, and/or the like. Alternatively, the input interface 43 may be provided for the gantry 10, for example. Further, the input interface 43 may be configured, for example, by using a tablet terminal or the like capable of wirelessly communicating with the main body of the console 40.

The processing circuitry 44 is configured to control operations of the entirety of the X-ray CT apparatus 1. For example, the processing circuitry 44 is configured to execute a system controlling function 441, a pre-processing function 442, a reconstruction processing function 443, and an image processing function 444.

The system controlling function 441 is configured to control various types of functions of the processing circuitry 44 on the basis of input operations received from the operator via the input interface 43. For example, the system controlling function 441 is configured to control a CT scan performed by the X-ray CT apparatus 1. Further, by controlling the pre-processing function 442, the reconstruction processing function 443, and the image processing function 444, the system controlling function 441 is configured to control processes of generating and displaying the CT image data performed on the console 40.

The pre-processing function 442 is configured to generate the projection data, by performing, on the detection data output from the DAS of the X-ray detector 12, pre-processing processes such as a logarithmic conversion process, an offset correcting process, an inter-channel sensitivity correcting process, and/or a beam hardening correction. In some situations, the data (the detection data) before the pre-processing processes and the data resulting from the pre-processing processes may collectively be referred to as projection data.

The reconstruction processing function 443 is configured to generate the CT image data (reconstructed image data) by performing a reconstructing process using a filter back-projection method, a successive approximation reconstruction method, or the like, on the projection data generated by the pre-processing function 442.

The image processing function 444 is configured to convert, on the basis of an input operation received from the operator via the input interface 43, the CT image data generated by the reconstruction processing function 443 into tomographic image data taken on an arbitrary cross-section or three-dimensional image data, by using a publicly-known method. Alternatively, the three-dimensional image data may directly be generated by the reconstruction processing function 443.

In this situation, for example, the processing circuitry 44 is realized by using one or more processors. In that situation, the processing functions included in the processing circuitry 44 are stored in the memory 41 in the form of computer-executable programs. Further, by reading and executing the programs from the memory 41, the processing circuitry 44 is configured to realize the functions corresponding to the programs. In other words, the processing circuitry 44 that has read the programs has the processing functions illustrated within the processing circuitry 44 in FIG. 1.

Although the example was explained above in which the single piece of processing circuitry (i.e., the processing circuitry 44) is configured to realize the processing functions described above, it is also acceptable, for example, to structure the processing circuitry 44 by combining together a plurality of independent processors, so that the processing functions are realized as a result of the processors executing the programs. Further, the processing functions included in the processing circuitry 44 may be realized as distributed among or integrated into one or more pieces of processing circuitry as appropriate. Furthermore, the processing functions included in the processing circuitry 44 may be realized by a combination of hardware such as circuitry and software. Furthermore, although the example was explained above in which the single memory (i.e., the memory 41) has stored therein the programs corresponding to the processing functions, possible embodiments are not limited to this example. For instance, it is also acceptable to provide a plurality of pieces of memory circuitry in a distributed manner, so that the processing circuitry 44 is configured to read and execute the corresponding programs from the individual pieces of memory circuitry.

An overall configuration of the X-ray CT apparatus 1 according to the present embodiment has thus been explained. With this configuration, the X-ray detector 12 in the present embodiment is structured by arranging a plurality of detector module units each of which is independent and individually replaceable.

Figure 2:
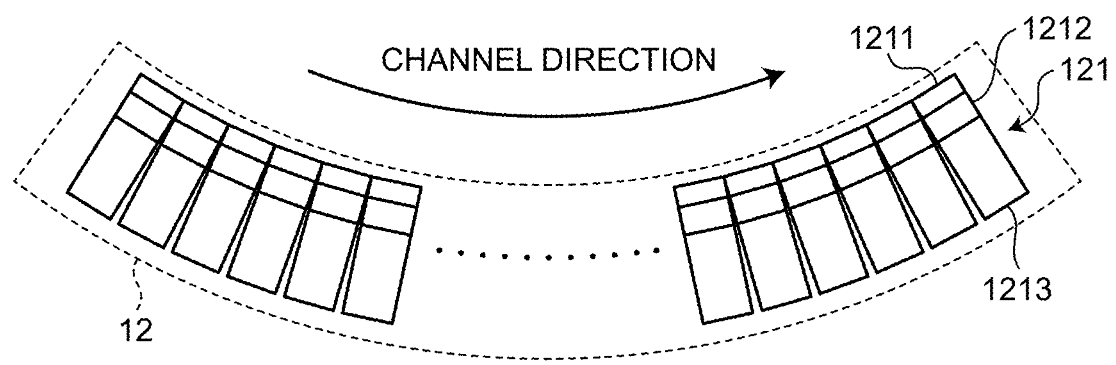
FIG. 2 is a drawing illustrating an exemplary configuration of an X-ray detector according to the first embodiment.

FIG. 2 is a drawing illustrating an exemplary configuration of the X-ray detector 12 according to the first embodiment.

For example, as illustrated in FIG. 2, the X-ray detector 12 is formed, as a whole, to have an arc shape along the channel direction and is fixed to the rotating frame 13 illustrated in FIG. 1, while being aligned in such a manner that the center of the arc matches the position of the X-ray tube 11. The axial direction of the arc of the X-ray detector 12 corresponds to the row direction, whereas the radial direction corresponds to the direction of the X-ray emissions.

Further, the X-ray detector 12 includes a plurality of detector module units 121 arranged in the channel direction.

The plurality of detector module units 121 are attached to a supporting member included in the X-ray detector 12, while being arranged in the channel direction. In this situation, the detector module units 121 are each configured so as to be independently attachable to and detachable from the supporting member. Each of the detector module units 121 includes a detector module 1211, a holding plate 1212, and a casing 1213.

The detector module 1211 includes a detecting element array in which the aforementioned plurality of detecting elements are arranged and the aforementioned signal processing circuitry, while being held by the holding plate 1212. The holding plate 1212 is arranged between the detector module 1211 and the casing 1213 and is fixed to the casing 1213 while holding the detector module 1211. The casing 1213 is configured to support the holding plate 1212 and houses therein a circuitry substrate on which the aforementioned DAS or the like is mounted.

Figure 3:
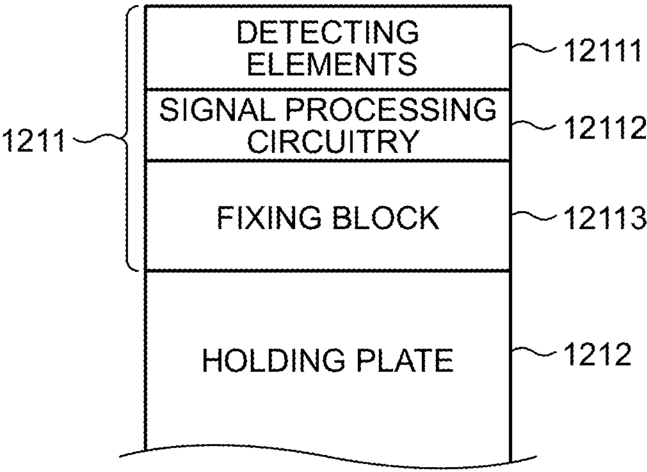
FIG. 3 is a diagram illustrating an exemplary configuration of a detector module according to the first embodiment.

FIG. 3 is a diagram illustrating an exemplary configuration of the detector module 1211 according to the first embodiment For example, as illustrated in FIG. 3, the detector module 1211 includes a plurality of detecting elements 12111 structuring the detecting element array, signal processing circuitry 12112, and a fixing block 12113.

The plurality of detecting elements 12111 are arranged on a surface of the signal processing circuitry 12112 and is electrically connected to the signal processing circuitry 12112. The signal processing circuitry 12112 is communicably connected to the circuitry substrate in the casing 1213, via a Flexible Printed Circuit (FPC) (not illustrated). The fixing block 12113 is configured to support the signal processing circuitry 12112 and is fixed to the holding plate 1212 by a fastening member such as a screw.

In the present embodiment, the fixing block 12113 and the holding plate 1212 are each formed by using a member having thermal conductivity. Further, the signal processing circuitry 12112 and the holding plate 1212 are thermally connected to each other via the fixing block 12113.

Generally speaking, in the detector module unit 121 structured as described above, it is considered that the signal processing circuitry 12112 included in the detector module 1211 generates heat in accordance with emission amounts of the X-rays emitted from the X-ray tube 11. Meanwhile, the detecting elements 12111 connected to the signal processing circuitry 12112 are usually set with a temperature upper limit, and the risk of failures increases as the temperature rises. Accordingly, in order to prevent the failures of the detecting elements 12111, it is necessary to cool the signal processing circuitry 12112.

Thus, the detector module unit 121 of the present embodiment has a cooling structure for cooling the signal processing circuitry 12112.

For instance, as an example of the cooling structure, it is possible to use a structure for cooling the signal processing circuitry 12112 in which, within the detector module unit 121, the holding plate 1212 holding the detector module 1211 is provided with fins, so as to ventilate the fins with air.

Figure 4A:
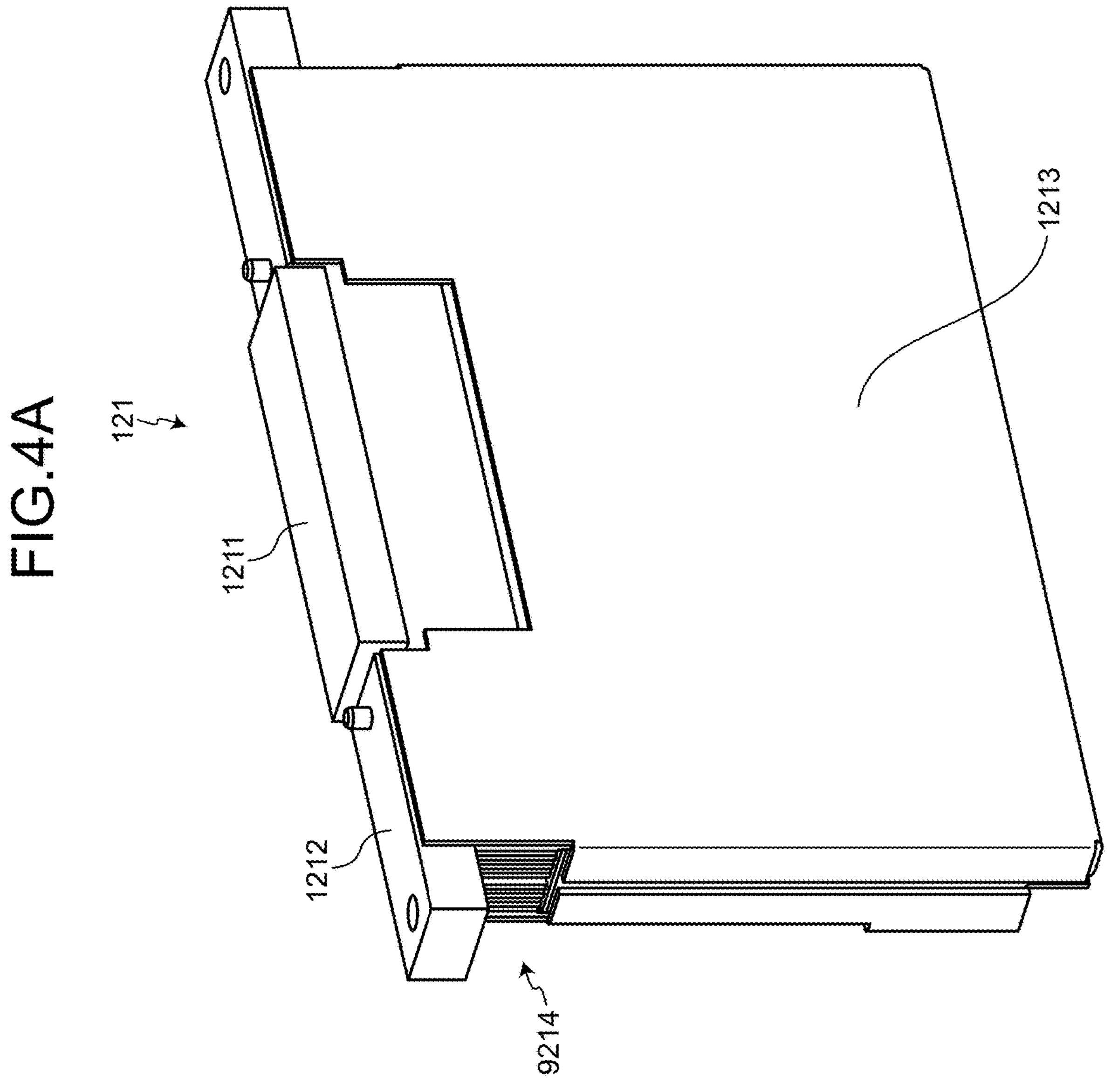
FIG. 4A is a drawing illustrating an exemplary configuration of a detector module unit according to a comparison example of the first embodiment.
Figure 4B:
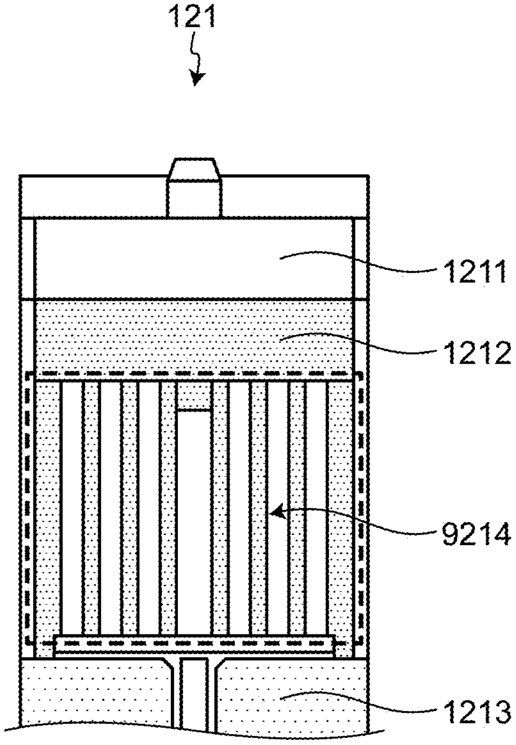
FIG. 4B is another drawing illustrating the exemplary configuration of the detector module unit according to the comparison example of the first embodiment.

FIGS. 4A and 4B are drawings illustrating an exemplary configuration of the detector module unit 121 according to a comparison example of the first embodiment. FIG. 4A is a perspective view illustrating the external appearance of the detector module unit 121 according to the comparison example of the first embodiment. FIG. 4B is a side view illustrating a cooling structure of the detector module unit 121 according to the comparison example of the first embodiment.

For example, as illustrated in FIGS. 4A and 4B, it is possible to use a structure in which, within the detector module unit 121, fins 9214 having a plurality of protrusion parts are provided so as to be positioned on the side of the holding plate 1212 closer to the casing 1213 while the holding plate 1212 holds the detector module 1211, so as to ventilate the spaces between the protrusion parts of the fins 9214 with cooling-purpose air. In FIG. 4B, the range indicated with the broken line is a cooling area formed by the fins 9214.

In such a cooling structure, however, because it is necessary to ventilate the small cooling area with the air, the heat dissipation area is so small that it is difficult to sufficiently cool the signal processing circuitry 12112. Further, when the heights of the fins 9214 are increased to enlarge the heat dissipation area, it would be inevitable to increase the length of the FPC connecting the detector module 1211 to the circuitry substrate in the casing 1213, which might lead to the possibility that quality of the signals might be deteriorated, and image quality might be degraded. Consequently, it is necessary to realize the cooling by transferring the heat generated by the signal processing circuitry 12112 to a wider range, in a location where the length of the FPC of the detector module 1211 is to not to be impacted.

For this reason, the detector module unit 121 according to the present embodiment is configured to be able to cool the signal processing circuitry 12112 more efficiently, by realizing the cooling where the heat generated by the signal processing circuitry 12112 is transferred to a wider range.

More specifically, in the present embodiment, the casing 1213 in the detector module unit 121 is thermally connected to the signal processing circuitry 12112 and has a first face and a second face opposing each other while the holding plate 1212 is interposed therebetween. In addition, the first face and the second face of the casing 1213 each have fins.

Next, an exemplary configuration of the detector module unit 121 according to the present embodiment will be explained in detail.

Figure 5A:
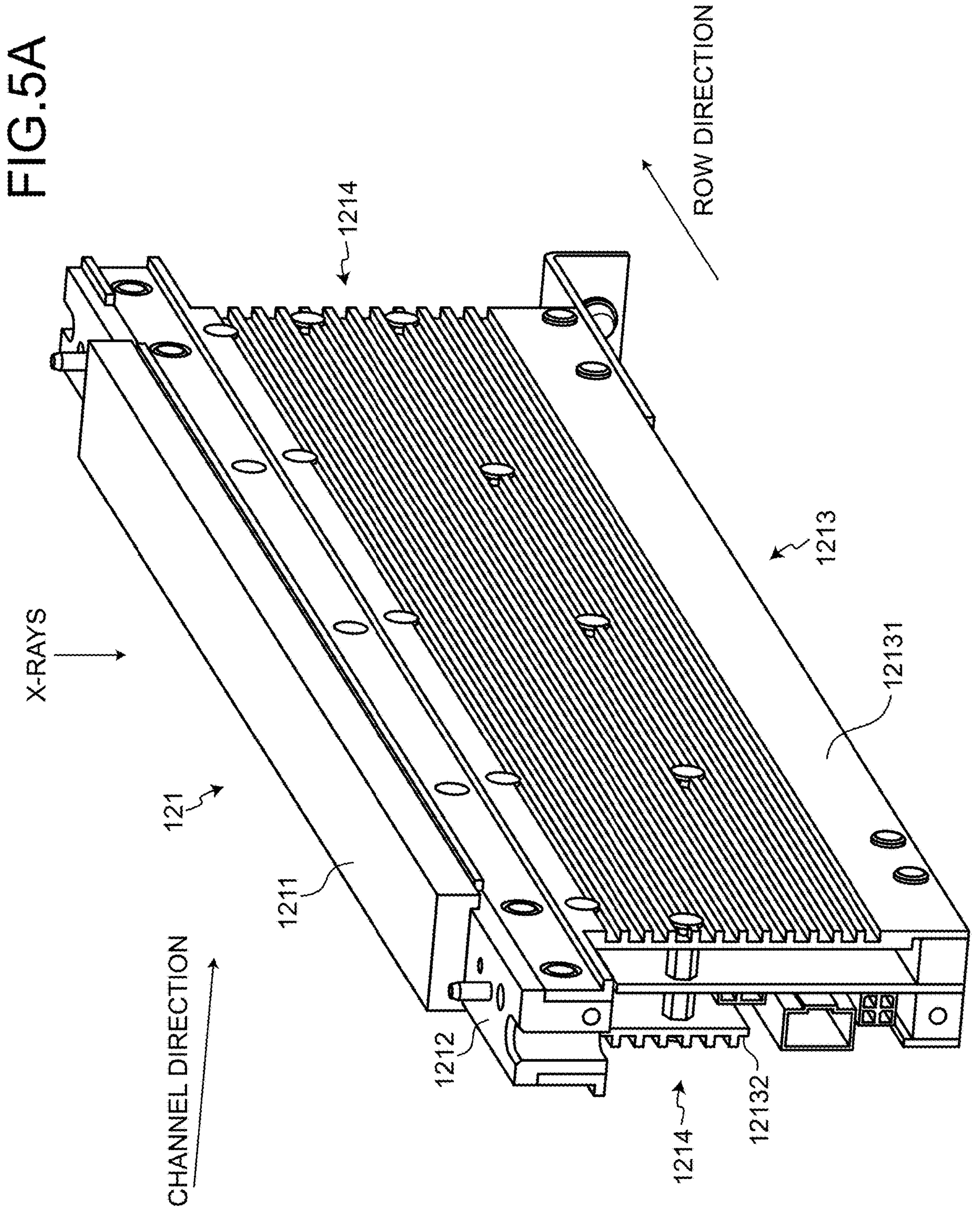
FIG. 5A is a drawing illustrating an exemplary configuration of a detector module unit according to the first embodiment.
Figure 5B:
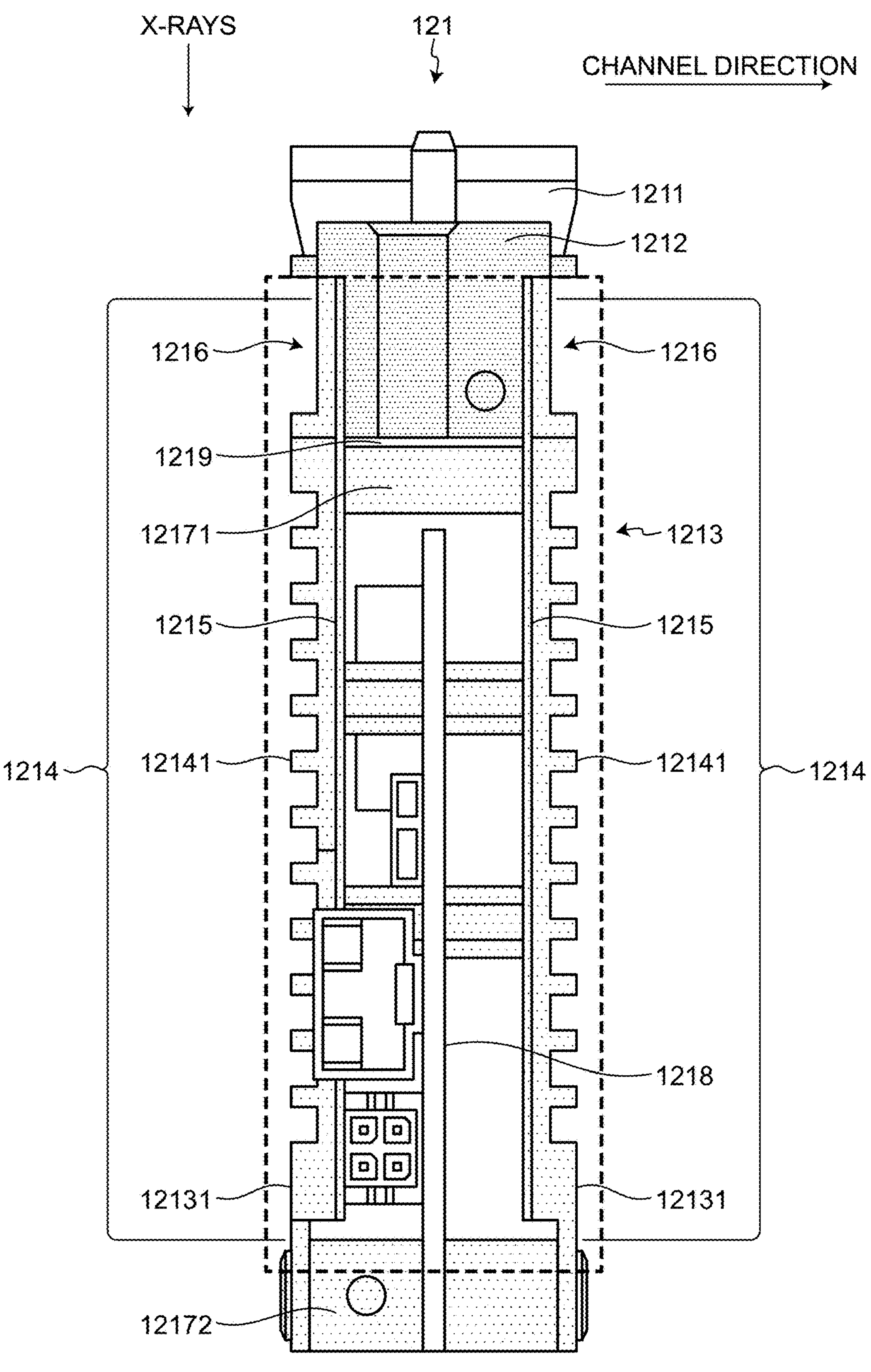
FIG. 5B is another drawing illustrating the exemplary configuration of the detector module unit according to the first embodiment.

FIGS. 5A and 5B are drawings illustrating an exemplary configuration of the detector module unit 121 according to the first embodiment. FIG. 5A is a perspective view illustrating the external appearance of the detector module unit 121 according to the first embodiment. FIG. 5B is a side view of the detector module unit 121 according to the first embodiment, as viewed in the row direction.

For example, as illustrated in FIGS. 5A and 5B, the detector module unit 121 according to the present embodiment includes the detector module 1211, the holding plate 1212, and the casing 1213.

In this situation, the casing 1213 as a whole is structured with a member having heat conductivity and is thermally connected to the holding plate 1212. As a result, the casing 1213 is thermally connected to the signal processing circuitry 12112 in the detector module 1211, via the holding plate 1212 and the fixing block 12113 illustrated in FIG. 3.

Further, the casing 1213 has a first face part 12131 and a second face part 12132 positioned so as to oppose each other while the holding plate 1212 is interposed therebetween. In this situation, the first face part 12131 is an example of the first face. The second face part 12132 is an example of the second face.

More specifically, the first face part 12131 and the second face part 12132 are positioned so as to sandwich lateral faces, in terms of the channel direction, of the holding plate 1212 from both sides, in an end part thereof positioned on the side closer to the detector module 1211, and are thermally connected to the holding plate 1212.

Further, in the present embodiment, fins 1214 having a plurality of protrusion parts 12141 are provided on the outer lateral face of each of the first face part 12131 and the second face part 12132. More specifically, the fins 1214 are provided on substantially the entirety of the outer lateral face of each of the first face part 12131 and the second face part 12132. Further, the plurality of protrusion parts 12141 included in the fins 1214 are each formed to have a bar-like shape extending in the slice direction and are arranged parallel to one another at predetermined intervals in the X-ray emission direction.

With the configuration described above, according to the present embodiment, for example, by an air blower or the like provided for the X-ray detector 12, the spaces between the protrusion parts 12141 of the fins 1214 provided on the first face part 12131 and the second face part 12132 of the casing 1213 are ventilated with cooling-purpose air. In FIG. 5B, the range indicated with the broken line is a cooling area formed by the fins 1214.

With this configuration, because the fins 1214 are provided on each of the two faces of the casing 1213 thermally connected to the signal processing circuitry 12112 of the detector module 1211, it is possible to secure a larger heat dissipation area, as compared to the situation where the holding plate 1212 is provided with fins as described in the above comparison example. Further, as compared to the situation where the holding plate 1212 is provided with the fins, because there is no need to increase the height of the holding plate 1212, it is possible to secure a larger heat dissipation area, without impacting the length of the FPC used for connecting the detector module 1211 to the circuitry substrate.

Consequently, according to the first embodiment, it is possible to realize the cooling by transferring the heat generated by the signal processing circuitry 12112 to a wider range and to thus more efficiently cool the signal processing circuitry 12112. In addition, it is possible to reduce the risk of the detecting elements 12111 failing due to the impact from the heat generated by the signal processing circuitry 12112 and to prevent the deterioration of the signal quality and the degradation of the image quality that might be caused if the FPC were prolonged.

The main configuration of the detector module unit 121 according to the first embodiment has thus been explained. In addition, the detector module unit 121 according to the present embodiment is further provided with the following configurations.

Specifically, in the present embodiment, the casing 1213 further includes heat transfer members having a high heat conduction rate and being provided on the first face and the second face.

For example, as illustrated in FIG. 5B, a graphite sheet 1215 having a high heat conduction rate is pasted on substantially the entirety of the inner lateral face of each of the first face part 12131 and the second face part 12132 of the casing 1213. Further, an end part of each of the first face part 12131 and the second face part 12132 positioned on the side closer to the detector module 1211 is thermally connected to the holding plate 1212 via the graphite sheet 1215. In this situation, the graphite sheet 1215 is an example of the heat transfer members.

With this configuration, it is possible to cool the signal processing circuitry 12112 even more efficiently.

Further, in the present embodiment, the casing 1213 further includes a rail-shaped member provided on the outer lateral face of each of the first and the second faces.

For example, as illustrated in FIG. 5B, a groove-like rail 1216 extending along the row direction is formed in an end part of the outer lateral face of each of the first face part 12131 and the second face part 12132 of the casing 1213, the end part being positioned closer to the detector module 1211. In this situation, on each of the first face part 12131 and the second face part 12132 of the casing 1213, the rail 1216 structures a part of the fins 1214 as being provided parallel to the protrusion parts 12141 included in the fins 1214. Further, when the detector module unit 121 is replaced, the rail 1216 is configured to guide moving of the detector module unit 121 in attachment/detachment directions, by sliding while being engaged with a replacement-purpose fixture or the like attached to a supporting member included in the X-ray detector 12. In this situation, the rail 1216 is an example of the rail-shaped member.

With this configuration, it is possible to utilize a part of the fins 1214 provided for the casing 1213, as a replacement mechanism used for replacing the detector module unit 121.

Further, in the present embodiment, the casing 1213 has a box-like shape structured by joining the first face and the second face together while using a joining member.

For example, as illustrated in FIG. 5B, the casing 1213 includes a first joining block 12171 arranged in an end part positioned closer to the holding plate 1212 and a second joining block 12172 arranged in an end part positioned farther from the holding plate 1212 and is structured by joining the first face part 12131 and the second face part 12132 together while using the first joining block 12171 and the second joining block 12172. With this configuration, the casing 1213 is formed to have the box-like shape in which the first face part 12131 and the second face part 12132 serve as lateral faces, while the first joining block 12171 and the second joining block 12172 serve as the top face and the bottom face. In this situation, the first joining block 12171 and the second joining block 12172 are each an example of the joining member. In an example, the joining member may be a stud or the like.

With the configurations described above, it is possible to configure the detector module unit 121 to have the box-like shape having a large cross-section coefficient, and it is therefore possible to enhance strength against centrifugal force caused when the X-ray tube 11 and the X-ray detector 12 are rotated by the rotating frame 13. As another aspect, it is possible to keep the detector module unit 121 light-weight, while maintaining the strength against the centrifugal force occurring at the time of the rotation.

Further, in the present embodiment, the detector module unit 121 further includes a circuitry substrate provided in the casing 1213 and a blocking member that blocks the X-rays from becoming incident to the circuitry substrate. The blocking member is positioned between the holding plate 1212 and the circuitry substrate and is held by a joining member.

For example, as illustrated in FIG. 5B, the detector module unit 121 includes a circuitry substrate 1218 provided in the casing 1213 and an X-ray blocking plate 1219 configured to block X-rays from becoming incident to the circuitry substrate 1218. The circuitry substrate 1218 includes electric power supply circuitry or the like for supplying electric power to the aforementioned DAS and to the signal processing circuitry 12112 of the detector module 1211. Further, the X-ray blocking plate 1219 is fixed to and held by the face of the first joining block 12171 on the side opposing the holding plate 1212, the first joining block 12171 being positioned between the holding plate 1212 and the circuitry substrate 1218. In this situation, the circuitry substrate 1218 is an example of the circuitry substrate. The X-ray blocking plate 1219 is an example of the blocking member.

With this configuration, because the casing 1213 is formed to have the box-like shape, by installing the X-ray blocking plate 1219 on the first joining block 12171 serving as the top face of the casing 1213, it is possible to easily realize the structure where the circuitry substrate 1218 is protected from the X-rays.

Modification Examples of First Embodiment

In the embodiment described above, the fins are provided on the first face and the second face of the casing 1213; however, possible embodiments are not limited to this example.

For instance, fins may further be provided on a lateral face of the holding plate 1212 facing the inside of the casing 1213. Further, fins may further be provided on a lateral face facing the inside of the casing 1213, of one or both of the first joining block 12171 and the second joining block 12172 included in the casing 1213.

With any of these configurations, by using the more fins, is possible to further enlarge the heat dissipation area and to further enhance the cooling efficiency for the signal processing circuitry 12112.

Further, in the above embodiment, the example was explained in which the X-ray detector 12 includes the plurality of detector module unit 121 arranged in the channel direction. In this configuration, the fins 1214 of adjacently-positioned detector module units 121 may be provided in such a manner that the protrusion parts 12141 included in the fins 1214 of one of the detector module units 121 (a first one of the detector module units) oppose the protrusion parts 12141 included in the fins 1214 of the other detector module unit 121 (a second one of the detector module units) or in such a manner that the protrusion parts 12141 included in the fins 1214 of one of the detector module units 121 oppose the gaps between the protrusion parts 12141 included in the fins 1214 of the other detector module unit 121.

For example, in the situation where the fins 1214 of the adjacently-positioned detector module units 121 are provided in such a manner that the protrusion parts 12141 included in the fins 1214 of one of the detector module units 121 oppose the gaps between the protrusion parts 12141 included in the fins 1214 of the other detector module unit 121, the cooling-purpose air flows more easily to the tip ends of the protrusion parts 12141 included in the fins 1214. With this configuration, it is possible to enhance cooling effects of the fins 1214, and it is therefore possible to further enhance cooling efficiency for the signal processing circuitry 12112.

Further, in the above embodiment, the example was explained in which the fins 1214 are provided on substantially the entirety of the outer lateral face of each of the first face part 12131 and the second face part 12132; however, possible embodiments are not limited to this example.

For instance, in the casing 1213, the amount of heat transferred from the signal processing circuitry 12112 is assumed to be larger in positions closer to the detector module 1211. Thus, for example, with respect to each of the first face part 12131 and the second face part 12132 of the casing 1213, it is also acceptable to provide the fins 1214 only on the side closer to the detector module 1211 where the amount of heat transferred from the signal processing circuitry 12112 is expected to be larger. Further, for example, the fins 1214 may be provided on the inner lateral face of each of the first face part 12131 and the second face part 12132 or may be provided on both the outer lateral face and the inner lateral face thereof.

Further, in the above embodiment, the example was explained in which the plurality of protrusion parts 12141 included in the fins 1214 are each formed to have the bar-like shape extending in the slice direction and are arranged parallel to one another at the predetermined intervals in the X-ray emission direction; however, possible embodiments are not limited to this example.

For instance, it is acceptable to increase the quantity of the protrusion parts 12141 on each of the first face part 12131 and the second face part 12132 of the casing 1213, in such a manner that the closer a position is to the detector module 1211, the smaller is the interval between the protrusion parts 12141 included in the fins 1214, because the closer positions are expected to have larger amounts of heat transferred from the signal processing circuitry 12112. Alternatively, for example, the protrusion parts 12141 may each be formed to have a bar-like shape extending in the X-ray emission direction, while being arranged parallel to one another at intervals in the slice direction.

Second Embodiment

In the first embodiment described above, the example was explained in which the first face and the second face of the casing 1213 of the detector module unit 121 each have the fins, as the cooling structure for cooling the signal processing circuitry 12112; however, possible examples of the cooling structure are not limited to this example.

For instance, the first face and the second face of the casing 1213 of the detector module unit 121 may each have a flow path for allowing a refrigerant such as cooling water to flow. In the following sections, this example will be explained as a second embodiment. In the second embodiment, differences from the first embodiment will primarily be explained. Detailed explanations of some of the features that are the same as those in the first embodiment will be omitted.

Figure 6A:
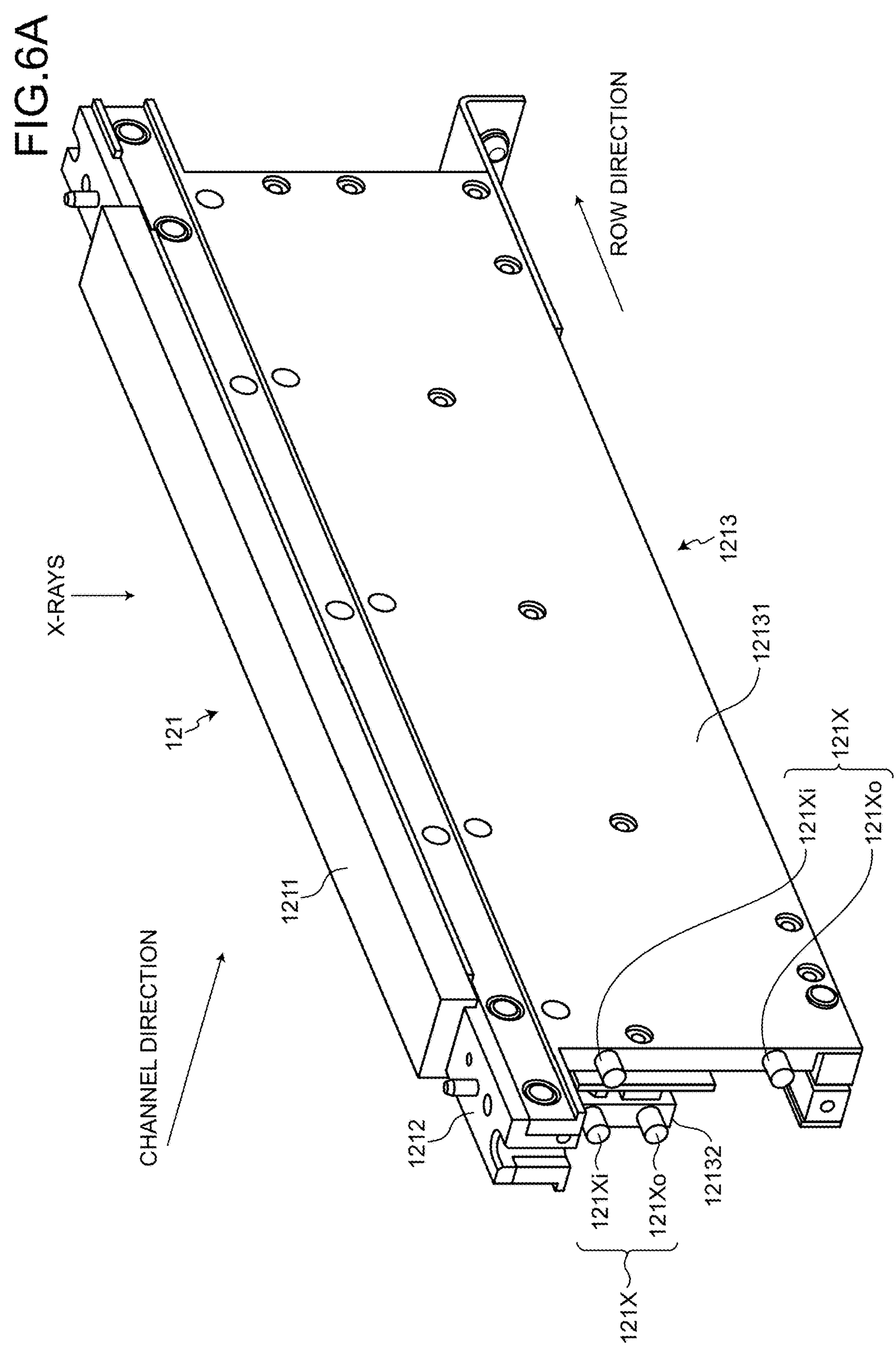
FIG. 6A is a drawing illustrating an exemplary configuration of a detector module unit according to a second embodiment.
Figure 6B:
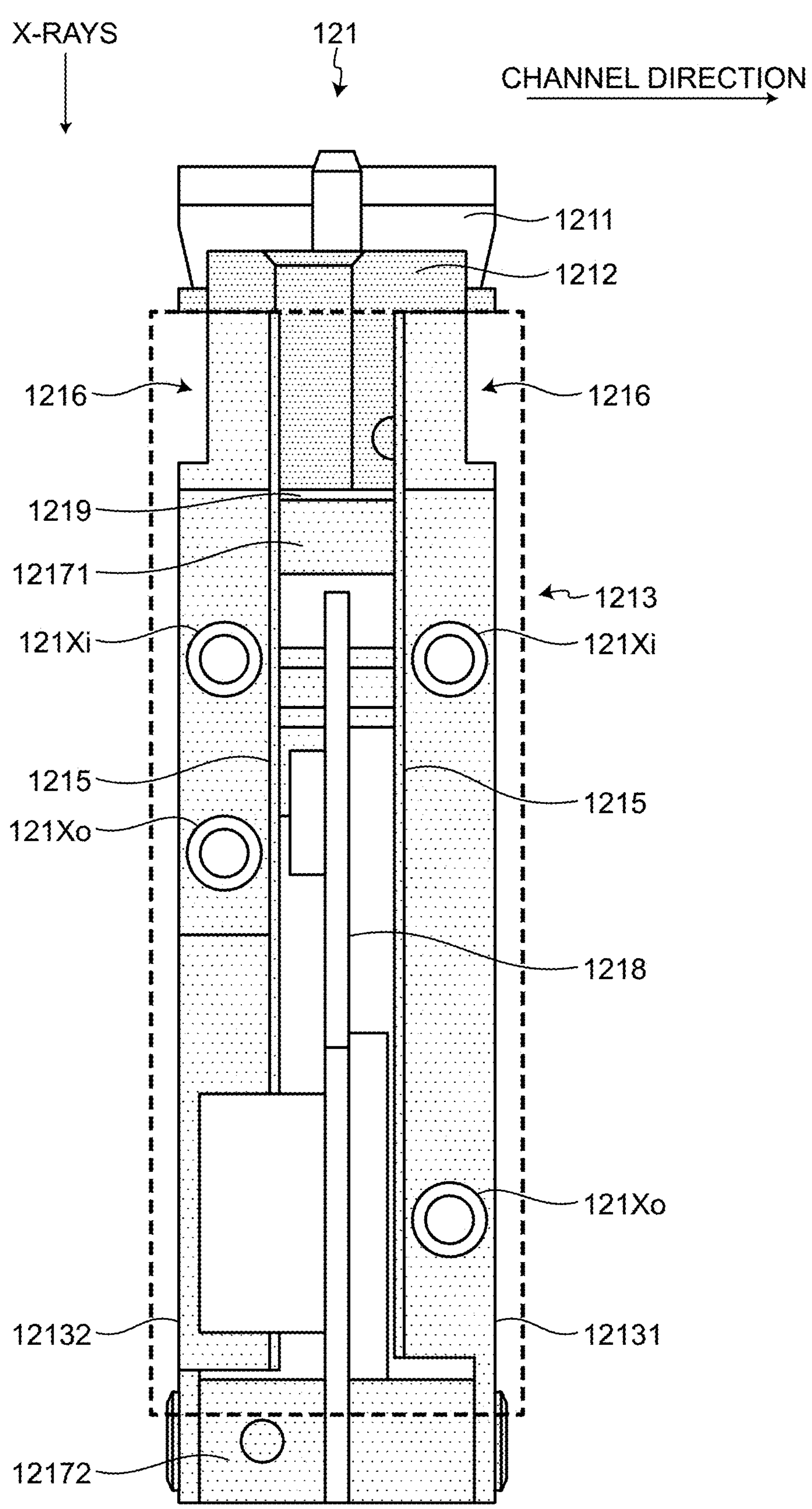
FIG. 6B is another drawing illustrating the exemplary configuration of the detector module unit according to the second embodiment.

FIGS. 6A and 6B are drawings illustrating an exemplary configuration of the detector module unit 121 according to the second embodiment. FIG. 6A is a perspective view illustrating the external appearance of the detector module unit 121 according to the second embodiment. FIG. 6B is a side view of the detector module unit 121 according to the second embodiment, as viewed in the row direction.

For example, as illustrated in FIGS. 6A and 6B, the detector module unit 121 according to the present embodiment includes the detector module 1211, the holding plate 1212, and the casing 1213.

In this situation, the casing 1213 as a whole is structured with a member having heat conductivity and is thermally connected to the holding plate 1212. As a result, the casing 1213 is thermally connected to the signal processing circuitry 12112 in the detector module 1211, via the holding plate 1212 and the fixing block 12113 illustrated in FIG. 3.

Further, the casing 1213 has the first face part 12131 and the second face part 12132 positioned so as to oppose each other while the holding plate 1212 is interposed therebetween. In this situation, the first face part 12131 is an example of the first face. The second face part 12132 is an example of the second face.

More specifically the first face part 12131 and the second face part 12132 are positioned so as to sandwich lateral faces, in terms of the channel direction, of the holding plate 1212 from both sides, in an end part thereof positioned on the side closer to the detector module 1211, and are thermally connected to the holding plate 1212.

Further, in the present embodiment, the first face part 12131 and the second face part 12132 each have, within the face part, a cooling pipe 121X embedded so as to allow a refrigerant such as cooling water to flow. In this situation, the cooling pipe 121X is an example of the flow path.

The cooling pipe 121X provided in the first face part 12131 is structured with an inlet 121Xi through which the refrigerant flows in, an outlet 121Xo through which the refrigerant flows out after flowing through the first face part 12131, and an inner cooling pipe that connects the inlet 121Xi to the outlet 121Xo.

In this situation, the inlet 121Xi is positioned on the side closer to the detector module 1211, whereas the outlet 121Xo is positioned on the side farther from the detector module 1211 than the inlet 121Xi is. Further, the inner cooling pipe is disposed so as to circle inside the first face part 12131 from the side closer to the detector module 1211 to the side farther from the detector module 1211. With this configuration, within the first face part 12131, the refrigerant flows through the side closer to the detector module 1211 and subsequently flows through the side farther from the detector module 1211.

Similarly, the cooling pipe 121X provided in the second face part 12132 is also provided in the same manner as the cooling pipe 121X provided in the first face part 12131. In other words, within the second face part 12132 also, the refrigerant flows through the side closer to the detector module 1211 and subsequently flows through the side farther from the detector module 1211.

As mentioned earlier, in the casing 1213, the amount of heat transferred from the signal processing circuitry 12112 is assumed to be larger in positions closer to the detector module 1211. Thus, as a result of providing the cooling pipes 121X in such a manner that the refrigerant flows through the side closer to the detector module 1211 and subsequently flows through the side farther from the detector module 1211, colder refrigerant flows through the positions having larger amounts of heat. It is therefore possible to efficiently cool wider ranges of the first face part 12131 and the second face part 12132.

With the configuration described above, because the cooling pipe 121X is provide in each of the two faces of the casing 1213 thermally connected to the signal processing circuitry 12112 of the detector module 1211, it is possible to secure a larger heat dissipation area as compared to the situation where, like in the comparison example described above, the holding plate 1212 is provided with fins. Further, as compared to the situation where the holding plate 1212 is provided with fins, because there is no need to increase the height of the holding plate 1212, it is possible to secure a larger heat dissipation area, without impacting the length of the FPC used for connecting the detector module 1211 to the circuitry substrate.

Consequently, according to the second embodiment, it is possible, similarly to the first embodiment, to realize the cooling by transferring the heat generated by the signal processing circuitry 12112 to a wider range and to thus more efficiently cool the signal processing circuitry 12112. In addition, it is possible to reduce the risk of the detecting elements 12111 failing due to the impact from the heat generated by the signal processing circuitry 12112 and to prevent the deterioration of the signal quality and the degradation of the image quality that might be caused if the FPC were prolonged.

Modification Examples of First and Second Embodiments

In the first and the second embodiments described above, the examples were explained in which the detector module unit and the radiation detector of the present disclosure are applied to the X-ray CT apparatus including the photon counting detector; however, possible embodiments are not limited to these examples. For instance, a detector module unit and a radiation detector of the present disclosure are similarly applicable to an X-ray CT apparatus including a detector of an integration-type (a current mode measuring scheme).

Further, there are various types of X-ray CT apparatuses such as a Rotate/Rotate-type (a third generation CT) in which an X-ray tube and a detector integrated together rotate around a subject and a Stationary/Rotate-type (a fourth generation CT) in which a large number of X-ray detecting elements arrayed in a ring formation are fixed, while only an X-ray tube rotates around a subject. A detector module unit and a radiation detector of the present disclosure are similarly applicable to any type of X-ray CT apparatus.

Further, in the first and the second embodiments described above, the examples were explained in which the detector module unit and the radiation detector according to the techniques disclosed in the present disclosure are applied to the X-ray detector of the X-ray CT apparatus; however, possible embodiments are not limited to these examples. For instance, a detector module unit and a radiation detector of the present disclosure are similarly applicable to other types of radiation detectors and radiation diagnosis apparatuses such as γ-ray detectors and PET apparatuses.

Further, the term "processor" used in the above explanations denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). When the processor is a CPU, for example, one or more processors are configured to realize the functions by reading and executing the programs saved in memory circuitry. In contrast, when the processor is an ASIC, for example, instead of having the programs saved in the memory circuitry, the functions are directly incorporated as logic circuitry in the circuitry of the one or more processors. The processors in the present embodiments do not each necessarily have to be structured as a single piece of circuitry. It is also acceptable to structure one processor by combining together a plurality of pieces of independent circuitry so as to realize the functions thereof. Further, it is also acceptable to integrate two or more of the constituent elements illustrated in FIG. 1 into one processor so as to realize the functions thereof.

Further, in the above embodiments and modification examples, the constituent elements of the apparatuses illustrated in the drawings are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

With regard to the processes explained in the above embodiments and modification examples, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to cool the signal processing circuitry more efficiently.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detector module unit comprising:

a detecting element array in which a plurality of detecting elements each configured to convert radiation into an electrical signal are arranged;

signal processing circuitry configured to process the electrical signals;

a holding plate configured to hold the detecting element array and the signal processing circuitry;

a casing that is thermally connected to the signal processing circuitry, wherein the casing has a first face and a second face, wherein the first face and the second face oppose each other while the holding plate is interposed therebetween;

a circuitry substrate disposed in the casing; and a blocking member configured to block radiation from becoming incident to the circuitry substrate, wherein the first face and the second face of the casing each have a fin, the casing has a box-like shape structured by joining the first face and the second face together while using a joining member, the joining member is positioned between the holding plate and the circuitry substrate, and the blocking member is held by the joining member.

2. The detector module unit according to claim 1, wherein the casing further includes heat transfer members having a high heat conduction rate and being provided on the first face and the second face.

3. The detector module unit according to claim 1, wherein the casing further has a rail-shaped member provided on an outer lateral face of each of the first and the second faces.

4. The detector module unit according to claim 1, wherein a fin is further provided on a lateral face of the holding plate facing an inside of the casing.

5. A radiation detector comprising:

a plurality of detector module units arranged in a channel direction, wherein as each of the plurality of detector module units, the radiation detector comprises the detector module unit according to claim 1.

6. The radiation detector according to claim 5, wherein, among the plurality of detector module units, the fins of adjacently-positioned detector module units are provided in such a manner that a protrusion part included in the fin of a first one of the detector module units opposes a gap between protrusion parts included in the fin of a second one of the detector module units.

7. An X-ray computed tomography apparatus comprising:

an X-ray tube configured to emit X-rays onto an examined subject; and an X-ray detector configured to detect X-rays that were emitted from the X-ray tube and have passed through the examined subject, wherein the X-ray computed tomography apparatus comprises the radiation detector according to claim 1 as the X-ray detector.

8. A detector module unit comprising:

a detecting element array in which a plurality of detecting elements each configured to convert radiation into an electrical signal are arranged;

signal processing circuitry configured to process the electrical signals;

a holding plate configured to hold the detecting element array and the signal processing circuitry;

a casing that is thermally connected to the signal processing circuitry, wherein the casing has a first face and a second face, wherein the first face and the second face oppose each other while the holding plate is interposed therebetween;

a circuitry substrate disposed in the casing; and a blocking member configured to block radiation from becoming incident to the circuitry substrate, wherein the first face and the second face of the casing each have a flow path, the casing has a box-like shape structured by joining the first face and the second face together while using a joining member, the joining member is positioned between the holding plate and the circuitry substrate, and the blocking member is held by the joining member.

* * * * *